(12) United States Patent
Lee et al.

(10) Patent No.: US 9,084,578 B2
(45) Date of Patent: Jul. 21, 2015

(54) DIAGNOSTIC IMAGING APPARATUS AND METHOD

(71) Applicant: Samsung Electronics Co., Ltd., Suwon-Si (KR)

(72) Inventors: Jong-Ha Lee, Yongin-si (KR); Yeong-Kyeong Seong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 176 days.

(21) Appl. No.: 13/792,621

(22) Filed: Mar. 11, 2013

(65) Prior Publication Data

US 2013/0245426 A1   Sep. 19, 2013

(30) Foreign Application Priority Data

Mar. 14, 2012  (KR) ..................... 10-2012-0026152

(51) Int. Cl.
| | |
|---|---|
| G06K 9/00 | (2006.01) |
| A61B 6/00 | (2006.01) |
| A61B 5/055 | (2006.01) |
| A61B 6/03 | (2006.01) |
| G06T 7/00 | (2006.01) |
| A61B 5/00 | (2006.01) |
| A61B 8/08 | (2006.01) |

(52) U.S. Cl.
CPC ................ *A61B 6/502* (2013.01); *A61B 5/055* (2013.01); *A61B 5/7257* (2013.01); *A61B 6/032* (2013.01); *A61B 6/5217* (2013.01); *G06T 7/0014* (2013.01); *A61B 8/085* (2013.01); *A61B 8/5223* (2013.01); *G06T 2207/10132* (2013.01); *G06T 2207/30068* (2013.01)

(58) Field of Classification Search
USPC ......... 382/100, 103, 106–107, 128–134, 154, 382/162, 168, 173, 181, 190, 199, 219, 232, 382/254, 274, 276, 280, 286–298, 305, 382/312; 600/408, 443, 439, 340; 378/4, 21
See application file for complete search history.

(56) References Cited

U.S. PATENT DOCUMENTS

| | | | | |
|---|---|---|---|---|
| 5,984,870 | A * | 11/1999 | Giger et al. | 600/443 |
| 6,246,782 | B1 * | 6/2001 | Shapiro et al. | 382/128 |
| 6,317,617 | B1 * | 11/2001 | Gilhuijs et al. | 600/408 |
| 2002/0003894 | A1 * | 1/2002 | Roehrig et al. | 382/128 |
| 2007/0167774 | A1 * | 7/2007 | Jeong et al. | 600/439 |
| 2011/0123119 | A1 * | 5/2011 | Yamanaka et al. | 382/190 |

FOREIGN PATENT DOCUMENTS

| | | |
|---|---|---|
| JP | 2003-189179 | 7/2003 |
| JP | 2010-158343 | 7/2010 |
| KR | 10-2007-0069322 | 7/2007 |

* cited by examiner

*Primary Examiner* — Seyed Azarian
(74) *Attorney, Agent, or Firm* — NSIP Law

(57) ABSTRACT

A diagnostic imaging apparatus and method are provided. The diagnostic imaging apparatus includes a detection unit configured to detect a lesion from a medical image, an interpretation unit configured to acquire a shape feature value by interpreting a shape of the detected lesion in a frequency domain, and a diagnosis unit configured to determine whether the detected lesion is benign or malignant based on the acquired shape feature value.

18 Claims, 6 Drawing Sheets

FIG. 1
REPLACEMENT SHEET
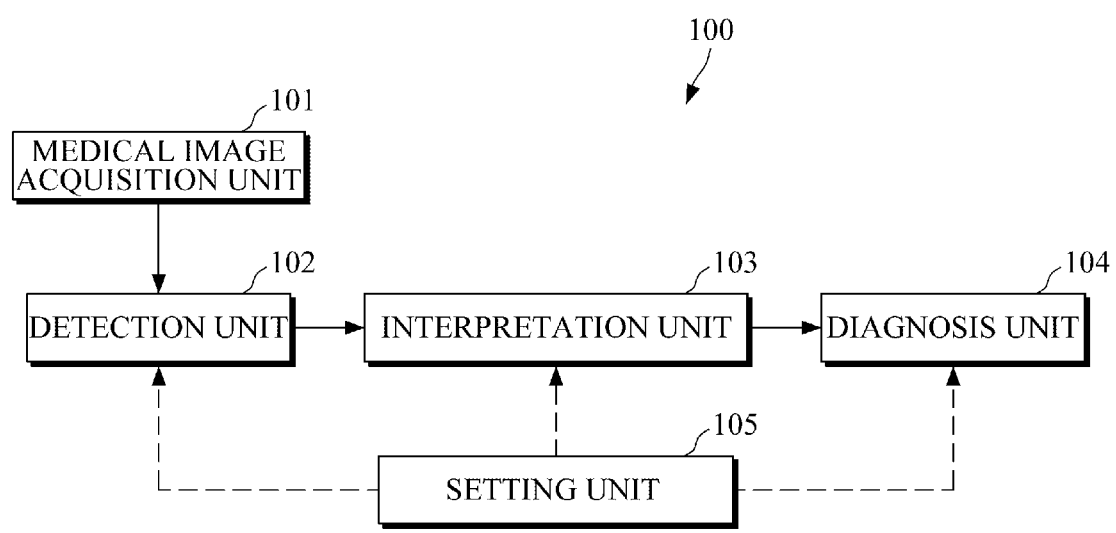

DIAGNOSTIC IMAGING APPARATUS AND METHOD

CROSS-REFERENCE TO RELATED APPLICATIONS

This application claims the benefit under 35 U.S.C. §119(a) of Korean Patent Application No. 10-2012-0026152, filed on Mar. 14, 2012, in the Korean Intellectual Property Office, the entire disclosure of which is incorporated herein by reference for all purposes.

BACKGROUND

1. Field

The following description relates to a diagnostic imaging apparatus and method.

2. Description of Related Art

Breast sonography is performed to detect masses or lesions that may not be detected by mammography, thereby reducing the need to perform biopsies that may prove to be unnecessary. A mass or lesion may be defined as a suspicious lump of tissues that differs from its surroundings. Women over the age of forty may benefit from breast sonography when mammography detects suspicious findings. Further, breast sonography is recommended for young, skinny women or pregnant women after mammography. The sensitivity of mammography is relatively low for women having dense breasts (for example, Asian women). In recent years, high-frequency probes have been developed for breast sonography. The resolution of sonograms has generally been improved because of the use of the high-frequency probes. In other words, breast sonography has played a significant role, especially for women with dense breasts, as a screening test for breast cancer.

In the meantime, the reading of breast mammograms and the detection of breast masses or lesions are performed according to the Breast Imaging-Reporting and Data System (BI-RDS) guidelines developed by the American College of Radiology (ACR). BI-RAD ultrasound findings include the shape of a lesion detected from a breast sonogram, the boundaries of the lesion, internal echoes, and rear echo shades. Malignant breast lesions are characterized by irregular shapes, lobular shapes, and irregular, rough internal echoes, whereas benign breast lesions are characterized by round shapes, smooth edges, and high, uniform internal echoes. Because cancer cells, unlike normal cells, experience continued growth and infiltrate into other tissues or organs, thereby resulting in lesions with irregular shapes, the shape of a lesion is a factor used to determine malignancy of the lesion. Internal echoes and rear echo shades are additional factors, but may be difficult to determine, especially in sonograms with significant noise or speckles.

The shape of a lesion may be defined as a morphological impression from the whole of a lesion. Lesions may be classified into four shape categories: round/oval, polygonal, lobulated, and irregular. Round/oval lesions are likely to be classified as benign, whereas polygonal, lobulated, or irregular lesions are likely to be classified as malignant. However, the interpretation of the shape of a lesion may be subjective and may thus vary depending on the radiologist. By converting the shape of lesions into numeric data, it is possible to implement a breast ultrasound-based computer-aided diagnosis system.

To properly interpret medical images, shape interpreters may be required. However, shape interpreters may not be able to adequately interpret medical images having significant speckle noise, such as sonograms. In addition, since shape interpreters are limited to the morphological distance and angle between shapes, it may be difficult to properly interpret highly irregular lesion shapes.

SUMMARY

In a general aspect, a diagnostic imaging apparatus includes a detection unit configured to detect a lesion from a medical image, an interpretation unit configured to acquire a shape feature value by interpreting a shape of the detected lesion in a frequency domain, and a diagnosis unit configured to determine whether the detected lesion is benign or malignant based on the acquired shape feature value.

The apparatus may further include that, to acquire the shape feature value, the interpretation unit is further configured to extract one or more feature points from boundaries of the detected lesion, generate a shape histogram based on the extracted feature points, and convert the shape histogram to the frequency domain.

The apparatus may further include that the interpretation unit is further configured to adjust a number of or an interval between the feature points to be extracted according to properties of the boundaries of the detected lesion.

The apparatus may further include that the interpretation unit is further configured to generate a multi-dimensional shape histogram based on the extracted feature points.

The apparatus may further include that the interpretation unit is further configured to generate the multi-dimensional shape histogram based on a polar diagram or a log-polar diagram.

The apparatus may further include that the interpretation unit is further configured to generate a Fourier coefficient by applying a Fourier transform to the shape histogram, and determine the Fourier coefficient as the shape feature value.

The apparatus may further include that the diagnosis unit is further configured to determine whether the lesion is benign or malignant by comparing the shape feature value with a model established by supervised learning.

The apparatus may further include that the medical image includes a radiograph, a sonogram, a magnetic resonance imaging (MRI) image, a computed tomography (CT) image, or any combination thereof.

The apparatus may further include that the interpretation unit includes a feature point extractor, a shape histogram generator, a Fourier transformer, and a shape feature value acquirer, the feature point extractor being configured to extract the feature points corresponding to boundaries of the detected lesion, the shape histogram generator being configured to generate the shape histogram based on the extracted feature points, the Fourier transformer being configured to transform the generated shape histogram into normalized Fourier coefficients to convert the generated shape histogram to the frequency domain, the shape feature value acquirer being configured to acquire the shape feature value from the normalized Fourier coefficients.

The apparatus may further include that the feature point extractor is further configured to sample pixels corresponding to the boundaries of the detected lesion to extract the feature points.

The apparatus may further include that the feature point extractor is further configured to extract feature points that are equally spaced from each other.

The apparatus may further include that the feature point extractor is further configured to extract a greater amount of feature points from a point on the boundaries of the lesion including a greater curvature than from a point on the boundaries of the lesion including a lesser curvature.

The apparatus may further include that the shape feature value acquirer is further configured to determine the normalized Fourier coefficients as the shape feature value to determine a shape of the detected lesion.

In another general aspect, a diagnostic imaging method includes detecting a lesion from a medical image, acquiring a shape feature value, the acquiring including interpreting a shape of the lesion in a frequency domain, and determining whether the detected lesion is benign or malignant based on the acquired shape feature value.

The method may further include that the acquiring further includes extracting one or more feature points from boundaries of the detected lesion, generating a shape histogram based on the extracted feature points, and converting the generated shape histogram to the frequency domain.

The method may further include that the converting of the generated shape histogram includes transforming the generated shape histogram into normalized Fourier coefficients.

The method may further include that the acquiring further includes determining the normalized Fourier coefficients as the shape feature value to determine a shape of the detected lesion.

The method may further include that the extracted feature points are equally spaced from each other.

The method may further include that a greater amount of the extracted feature points is from a point on the boundaries of the lesion including a greater curvature than from a point on the boundaries of the lesion including a lesser curvature.

Other features and aspects may be apparent from the following detailed description, the drawings, and the claims.

BRIEF DESCRIPTION OF THE DRAWINGS

FIG. 1 is a diagram illustrating an example of a diagnostic imaging apparatus.

Figure 2:
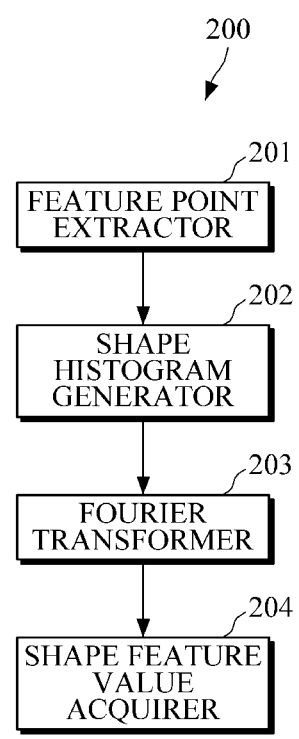
FIG. 2 is a diagram illustrating an example of an interpretation unit of the diagnostic imaging apparatus of FIG. 1.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. Also, descriptions of well-known functions and constructions may be omitted for increased clarity and conciseness.

FIG. 1 is a diagram illustrating an example of a diagnostic imaging apparatus.

Referring to the example illustrated in FIG. 1, a diagnostic imaging apparatus 100 includes a medical image acquisition unit 101, a detection unit 102, an interpretation unit 103, a diagnosis unit 104, and a setting unit 105.

The medical image acquisition unit 101 acquires a medical image. In an example, the acquired medical image is one or more of the group consisting of a radiograph, a sonogram, a magnetic resonance imaging (MRI) image, and a computed tomography (CT) image. Moreover, in a further example, the acquired medical image is a two-dimensional (2D) image or a three-dimensional (3D) image.

The detection unit 102 detects a lesion, i.e., a mass different from surrounding tissues, from the acquired medical image provided by the medical image acquisition unit 101. In an example, the detection unit 102 detects a lesion that is suspected to be cancerous or tumorous from the acquired medical image.

In a general aspect, the detection unit 102 detects a lesion from the acquired medical image based on an automatic lesion detection algorithm, for example, a Sobel edge detector, or the location of the lesion received from a user.

The interpretation unit 103 acquires one or more shape feature values by interpreting the shape of the detected lesion in a frequency domain. The term "shape feature value", in an example used herein, is feature information corresponding to the shape of a lesion, and indicates the shape of a lesion in a frequency domain. In another example, the interpretation unit 103 acquires the shape feature values by extracting one or more feature points from the boundaries of the detected lesion (including the boundary lines or boundary interfaces of the detected lesion), generating a shape histogram based on the extracted feature points, and converting the generated shape histogram to a frequency domain.

The diagnosis unit 104 determines whether the detected lesion is benign or malignant based on the shape feature values acquired by the interpretation unit 103. In an example, the diagnosis unit 104 determines whether the detected lesion is benign or malignant by comparing the acquired shape feature values with a previously established model through supervised learning.

In a general aspect, the setting unit 105 sets various parameters for the detection unit 102, the interpretation unit 103, the diagnosis unit 104, or any combination thereof. For example, the setting unit 105 sets a number of and a distance between feature points to be extracted from the boundaries of the detected lesion for the detection unit 102. In an additional example, the setting unit 105 sets a number of shape feature values to be acquired and a detailed interpretation policy for the interpretation unit 103. In another example, the setting unit 105 sets a model and a period of learning for the diagnosis unit 104.

FIG. 2 is a diagram illustrating an example of the interpretation unit 103 of the diagnostic imaging apparatus of FIG. 1.

Referring to the example illustrated in FIG. 2, an interpretation unit 103 includes a feature point extractor 201, a shape histogram generator 202, a Fourier transformer 203, and a shape feature value acquirer 204.

As illustrated in FIGS. 1 and 2, in a general aspect, the feature point extractor 201 extracts a plurality of feature points by sampling pixels corresponding to the boundaries of a lesion detected by the detection unit 102. In an example, the number of and the distance between feature points extracted by the feature point extractor 201 is adjusted by the setting unit 105. In a further example, the feature point extractor 201 extracts one or more feature points from the boundaries of a lesion such that the feature points are equally spaced. As another example, the feature point extractor 201 adjusts the sampling interval such that a greater amount of feature points is extracted from a point on the boundaries of a lesion with a larger curvature than from a point on the boundaries of the lesion with a smaller curvature.

The shape histogram generator 202 generates a shape histogram based on the feature points extracted by the feature point extractor 201. In an example, a shape histogram renders a lesion in a predefined space and shows the distribution of feature elements of the shape of the lesion. In another example, the shape histogram generator 202 generates a 2D shape histogram or a three or more-dimensional shape histogram depending on the type or the characteristics of a lesion. In a further example, in response to a given medical image being a 2D image, the feature point extractor 201 extracts one or more feature points from the boundaries of a lesion detected from the 2D image, and the shape histogram generator 202 generates a 2D shape histogram showing the distribution of the extracted feature points on a 2D plane. As an additional example, in response to the given medical image being a 3D image, the feature point extractor 201 extracts one or more feature points from the boundaries of a lesion detected from the 3D image, and the shape histogram generator 202 generates a 3D shape histogram showing the distribution of the extracted feature points in a 3D space.

The shape histogram generator 202 is not restricted to generating a shape histogram via a certain method. In an example, the shape histogram generator 202 generates a shape histogram by arranging one or more extracted feature points over a polar diagram or a log-polar diagram and normalizing the number of feature points included in each region (for example, each bin) in the polar diagram or the log-polar diagram.

In a general aspect, the Fourier transformer 203 performs a Fourier transform on the shape histogram generated by the shape histogram generator 202. For example, in response to the shape histogram generator 202 generating a 2D shape histogram, the Fourier transformer 203 converts the 2D shape histogram into a one-dimensional (1D) histogram signal and performs Fast Fourier Transform (FFT) on the 1D histogram signal. As another example, in the case of a 3D shape histogram, the Fourier transformer 203 converts the 3D shape histogram into a 2D histogram signal and performs FFT on the 2D histogram signal.

In a general aspect, the shape feature value acquirer 204 acquires one or more shape feature values based on computation results provided by the Fourier transformer 203. For example, the shape feature value acquirer 204 determines Fourier coefficients obtained by the Fourier transform operation performed by the Fourier transformer 203 as shape feature values.

In a general aspect, the diagnostic imaging apparatus 100 illustrated in FIG. 1 or the interpretation unit 200 illustrated in FIG. 2 is divided into one or more units or elements according to a different set of rules from those set forth herein. In an example, two or more function units are incorporated into a single unit, or the functions of a function unit are configured to be performed by two or more function units.

Figure 3:
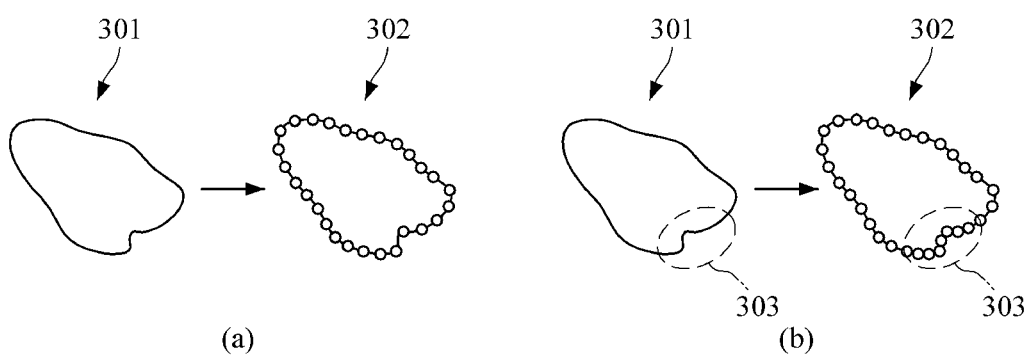
FIG. 3 is a diagram illustrating an example of a method of extracting a feature point.

FIG. 3 is a diagram illustrating an example of a method of extracting a feature point.

Referring to the examples illustrated in FIGS. 2 and 3, the feature point extractor 201 extracts a plurality of feature points 302 from a boundary 301 of a lesion. Though the lesion boundary 301 is illustrated in FIG. 3 as a line, in another example, it may be rendered in various shapes other than a line shape, such as, for example, a multi-dimensional shape, such as a plane or a space.

In a general aspect, the feature point extractor 201 adjusts the number of and the interval between feature points to be extracted according to the properties of the lesion boundary 301. For example, the feature point extractor 201 extracts the feature points 302 such that the feature points 302 are equally spaced, as illustrated in FIG. 3(*a*). In a further example, the feature point extractor 201 extracts the feature points 302 such that more feature points may be extracted from a part 303 on the lesion boundary 301 with a relatively greater curvature than from the rest of the lesion boundary 301, as illustrated in FIG. 3(*b*).

Figure 4:
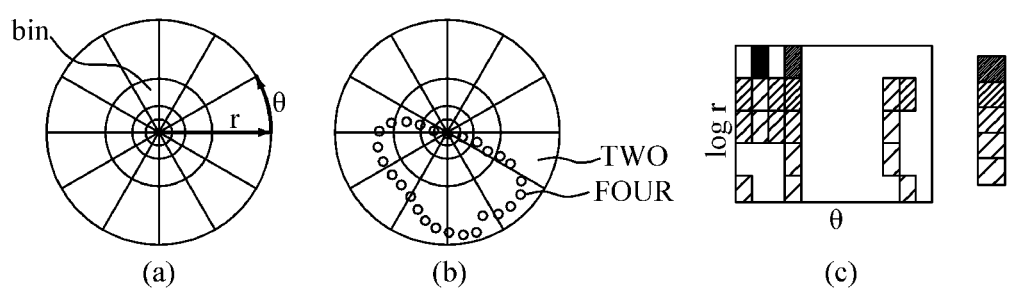
FIG. 4 is a diagram illustrating an example of a method of generating a shape histogram.

FIG. 4 is a diagram illustrating an example of a method of generating a shape histogram.

The shape histogram generator 202 defines a log-polar diagram as illustrated in FIGS. 2 and 4(*a*). The log-polar diagram divides a particular plane (or space) into a number of "bin"s according to the length "r" and the angle "θ". For example, each bin may be defined in the log-polar diagram along r's and θ's with respect to the center of the log-polar diagram. In an example, the type of diagram used by the shape histogram generator 202 and the number of bins defined in the corresponding diagram are set by the setting unit 105 as illustrated in FIG. 1.

The shape histogram generator 202 arranges one or more feature points over the log-polar diagram as illustrated in FIG. 4(*b*).

The shape histogram generator 202 generates a shape histogram based on the number of feature points included in each bin of the log-polar diagram as illustrated in FIG. 4(*b*). In an example, the shape histogram generator 202 sets a reference point in the log-polar diagram illustrated in FIG. 4(*b*). In another example, the reference point is the center of the distribution of feature points in the log-polar diagram or is a point populated with feature points. A preferable position of a reference point is dependent on the type of a given medical image. As such, in an example, the setting unit 105 sets the position of the reference point. In a further example, once the reference point is set, the shape histogram generator 202 records the number of feature points included in each bin in the log-polar diagram and generates a 2D shape histogram with "r" and "θ" as the X- and Y-axes, respectively, based on the number of feature points included in each bin in the log-polar diagram. In an additional example, each cell in the generated 2D shape histogram is filled with different colors according to the number of feature points.

In another general aspect, the shape histogram generator 202 uses various manners other than the manner using the log-polar diagram to divide a plane or a space. In addition, the shape histogram generator 202 may not only generate 2D shape histograms, but also generate 3D shape histograms. In an example, in the case of a 3D medical image, as the feature points exist in a 3D space, the shape histogram generator 202 arranges feature points in the 3D space and generates a 3D shape histogram based on the number of the feature points included in each cell of the 3D space.

Figure 5:
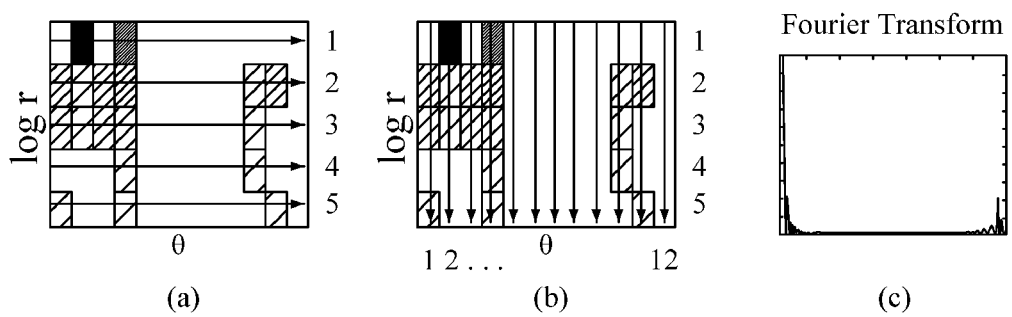
FIG. 5 is a diagram illustrating an example of a method of acquiring a shape feature value.

FIG. 5 is a diagram illustrating an example of a method of acquiring a shape feature value.

Referring to the examples illustrated in FIGS. 2, 5(*a*) and 5(*b*), the Fourier transformer 203 generates a 1D histogram signal by scanning a 2D shape histogram from the left to the right or from the top to the bottom. In an aspect, FFT converts the 1D histogram signal into a combination of various frequencies from lower frequencies to higher frequencies. The Fourier transformer 203 calculates and normalizes Fourier coefficients as illustrated in FIG. 5(*c*).

In a general aspect, the shape feature value acquirer 204 determines the normalized Fourier coefficients as shape feature values to determine the shape of a lesion. As the number of frequencies increases, the Fourier coefficients additionally increase, thereby increasing the number of identifiers to interpret the shape of a lesion. A larger amount of frequencies used in Fourier transforms enables a more precise interpretation of the shape of a lesion, while subsequently requiring a larger amount of computation to arrive at that more precise interpretation. In an example, a preferable number of frequencies to be used in a Fourier transform is adjusted by the setting unit 105.

In another general aspect, the Fourier transformer 203 and the shape feature value acquirer 204 generate a 2D histogram using a previously scanned 3D shape histogram, convert the 2D histogram signal into a 1D histogram signal, and calculate Fourier coefficients.

Referring back to the example illustrated in FIG. 1, in still another aspect, the diagnosis unit 104 acquires a lesion shape pattern model by "supervised machine learning" based on the shape feature values acquired by the shape feature value acquirer 204. In an example, the shape feature value of each image stored in a given image database is acquired by calculating the Fourier coefficient of each image. Thereafter, in this example, a lesion shape pattern model is established by applying these shape feature values to a supervised machine learning unit. In a further example, the model is used to interpret the shape of a lesion detected from a new image and determine whether the detected lesion is benign and malignant. For example, a supervised learning algorithm such as Support Vector Machine (SVM) is used to establish the model.

Figure 6:
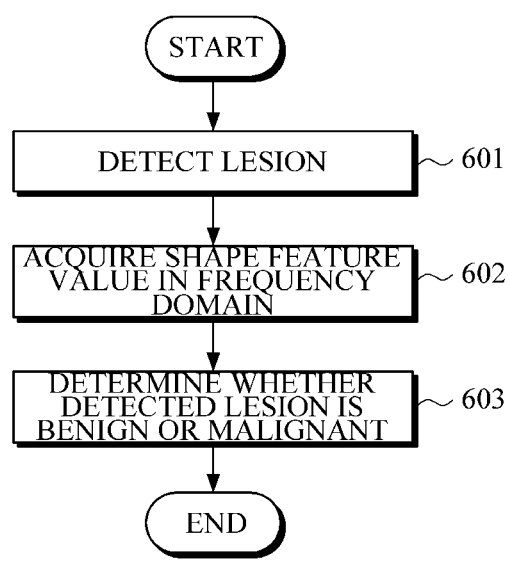
FIG. 6 is a flowchart illustrating an example of a diagnostic imaging method.

FIG. 6 is a flowchart illustrating an example of a diagnostic imaging method.

Referring to the examples illustrated in FIGS. 1 and 6, a lesion is detected (601) from a medical image.

In an example, the detection unit 102 detects a suspected cancer lesion from a sonogram.

A shape feature value in a frequency domain is acquired (602) as information relating to the shape of the detected lesion. In an example, the interpretation unit 103 acquires the shape feature value by extracting one or more feature points from the boundaries of the detected lesion, generating a shape histogram corresponding to the distribution of the extracted feature points in a particular space, and converting the generated shape histogram to the frequency domain.

A determination (603) is made as to whether the detected lesion is benign or malignant based on the acquired shape feature value. In an example, the diagnosis unit 104 determines whether the detected lesion is benign or malignant by comparing the acquired shape feature value with a previously-established model.

The units described herein may be implemented using hardware components, such as, for example, microphones, amplifiers, band-pass filters, audio to digital convertors, and processing devices, and software components. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an OS and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums.

In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Further, the described unit to perform an operation or a method may be hardware, software, or some combination of hardware and software. For example, the unit may be a software package running on a computer or the computer on which that software is running.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A diagnostic imaging apparatus, comprising:
   a detection unit configured to detect a lesion from a medical image;
   an interpretation unit configured to
      acquire a shape feature value by interpreting a shape of the detected lesion in a frequency domain;
      extract one or more feature points from boundaries of the detected lesion; and
      adjust a number of or an interval between the feature points to be extracted according to properties of the boundaries of the detected lesion; and
   a diagnosis unit configured to determine whether the detected lesion is benign or malignant based on the acquired shape feature value.

2. The diagnostic imaging apparatus of claim 1, wherein, to acquire the shape feature value, the interpretation unit is further configured to generate a shape histogram based on the extracted feature points and convert the shape histogram to the frequency domain.

3. The diagnostic imaging apparatus of claim 2, wherein the interpretation unit is further configured to generate a multi-dimensional shape histogram based on the extracted feature points.

4. The diagnostic imaging apparatus of claim 3, wherein the interpretation unit is further configured to generate the multi-dimensional shape histogram based on a polar diagram or a log-polar diagram.

5. The diagnostic imaging apparatus of claim 2, wherein the interpretation unit is further configured to generate a Fourier coefficient by applying a Fourier transform to the shape histogram, and determine the Fourier coefficient as the shape feature value.

6. The diagnostic imaging apparatus of claim 2, wherein the interpretation unit comprises a feature point extractor, a shape histogram generator, a Fourier transformer, and a shape feature value acquirer, the feature point extractor being configured to extract the feature points corresponding to boundaries of the detected lesion, the shape histogram generator being configured to generate the shape histogram based on the extracted feature points, the Fourier transformer being configured to transform the generated shape histogram into normalized Fourier coefficients to convert the generated shape histogram to the frequency domain, the shape feature value acquirer being configured to acquire the shape feature value from the normalized Fourier coefficients.

7. The diagnostic imaging apparatus of claim 6, wherein the feature point extractor is further configured to sample pixels corresponding to the boundaries of the detected lesion to extract the feature points.

8. The diagnostic imaging apparatus of claim 6, wherein the feature point extractor is further configured to extract feature points that are equally spaced from each other.

9. The diagnostic imaging apparatus of claim 6, wherein the feature point extractor is further configured to extract a greater amount of feature points from a point on the boundaries of the lesion comprising a greater curvature than from a point on the boundaries of the lesion comprising a lesser curvature.

10. The diagnostic imaging apparatus of claim 6, wherein the shape feature value acquirer is further configured to determine the normalized Fourier coefficients as the shape feature value to determine a shape of the detected lesion.

11. The diagnostic imaging apparatus of claim 1, wherein the diagnosis unit is further configured to determine whether the lesion is benign or malignant by comparing the shape feature value with a model established by supervised learning.

12. The diagnostic imaging apparatus of claim 1, wherein the medical image comprises a radiograph, a sonogram, a magnetic resonance imaging (MRI) image, a computed tomography (CT) image, or any combination thereof.

13. A diagnostic imaging method, comprising:
    detecting, using a detection unit, a lesion from a medical image;
    acquiring using an interpretation unit, a shape feature value, the acquiring comprising interpreting a shape of the lesion in a frequency domain;
    extracting, using the interpretation unit, one or more feature points from boundaries of the detected lesion;
    adjusting, using the interpretation unit, a number of or an interval between the feature points to be extracted according to properties of the boundaries of the detected lesion; and
    determining, using a diagnosis unit, whether the detected lesion is benign or malignant based on the acquired shape feature value.

14. The diagnostic imaging method of claim 13, wherein the acquiring further comprises generating a shape histogram based on the extracted feature points and converting the generated shape histogram to the frequency domain.

15. The diagnostic imaging method of claim 14, wherein the converting of the generated shape histogram comprises transforming the generated shape histogram into normalized Fourier coefficients.

16. The diagnostic imaging method of claim 14, wherein the acquiring further comprises determining the normalized Fourier coefficients as the shape feature value to determine a shape of the detected lesion.

17. The diagnostic imaging method of claim 14, wherein the extracted feature points are equally spaced from each other.

18. The diagnostic imaging method of claim 14, wherein a greater amount of the extracted feature points is from a point on the boundaries of the lesion comprising a greater curvature than from a point on the boundaries of the lesion comprising a lesser curvature.

* * * * *